United States Patent [19]

Koundakjian

[11] 4,218,444

[45] Aug. 19, 1980

[54] INSECTICIDAL FORMULATION

[75] Inventor: Theodore H. Koundakjian, Albany, Calif.

[73] Assignee: Chevron Research Company, San Francisco, Calif.

[21] Appl. No.: 912,777

[22] Filed: Jun. 5, 1978

[51] Int. Cl.$^2$ .............................................. A01N 9/36
[52] U.S. Cl. ...................................... 424/212; 424/220
[58] Field of Search ................................ 424/220, 212

[56] References Cited

U.S. PATENT DOCUMENTS

| | | | |
|---|---|---|---|
| 1,707,465 | 4/1929 | Volck | 424/171 |
| 1,707,468 | 4/1929 | Volck | 424/171 |
| 3,309,266 | 3/1967 | Magee | 424/220 |
| 3,676,555 | 7/1972 | Schrader et al. | 424/220 |
| 3,716,600 | 2/1973 | Magee | 424/212 |
| 3,845,172 | 10/1974 | Magee | 424/220 X |

*Primary Examiner*—V. D. Turner
*Attorney, Agent, or Firm*—D. A. Newell; T. G. DeJonghe

[57] ABSTRACT

An insecticidal formulation comprising: (1) acephate or acephatemet; (3) a hydrocarbon component having a boiling range at 10 mm Hg absolute pressure substantially within the range of 550° to 950° F. and an unsulfonated residue above about 85 weight percent; (3) a bridging component in an amount effective to form a solution containing the aforesaid two components, wherein the bridging component is isopropyl alcohol, secondary butyl alcohol, tertiary butyl alcohol, or methylene chloride.

9 Claims, No Drawings

INSECTICIDAL FORMULATION

BACKGROUND OF THE INVENTION

The present invention relates to an insecticidal formulation containing a phosphoroamidothioate and an oil.

The use of phosphoroamidothioates as insecticides is disclosed in U.S. Pat. Nos. 3,309,266 and 3,716,600.

The use of oils as insecticides is disclosed in several patents which have issued to William Hunter Volck, and the subject insecticidal oil compositions of these patents are commonly referred to as Volck oils, "VOLCK" being a registered trademark of Chevron Chemical Company. Particular reference is made to the following Volck patents: U.S. Pat. Nos. 1,707,465; 1,707,466; 1,707,467; and 1,707,468. These reference patents point out that it is desirable for the oil to have a low unsaturates content. Means for reducing the unsaturate content of these high-boiling viscous oils which are to be used as insecticides are disclosed in U.S. Pat. Nos. 2,047,055 and 2,076,105.

For certain purposes, it has been found desirable to combine insecticidal phosphoroamidothioates and viscous oils to obtain an improved insecticidal formulation. However, such combination, particularly in reasonably stable form, is not easy to achieve, owing to the characteristics of the phosphoroamidothioates of not being soluble in viscous oils and not being stable in many solvents that might otherwise be desirable.

The use of oil to improve the effectiveness of insecticides is disclosed in "The Chemistry and Action of Insecticides" by Harold H. Shepard, McGraw-Hill Book Company, Inc., 1951, at page 202.

SUMMARY OF THE INVENTION

According to the present invention, an insecticidal formulation is provided which comprises: (1) acephate or acephatemet; (2) a paraffinic hydrocarbon component having a boiling range at 10 mm Hg absolute pressure substantially within the range of 550° to 950° F. and an unsulfonated residue above about 85 weight percent; and (3) a bridging component in an amount effective to form a solution containing the aforesaid two components, wherein the bridging component is isopropyl alcohol, secondary butyl alcohol, tertiary butyl alcohol, or methylene chloride.

"Acephate" is the common name for the insecticide O,S-dimethyl-N-acetylphosphoroamidothioate. This insecticide and its preparation are disclosed in U.S. Pat. No. 3,716,600.

"Acephatemet" is the common name for the insecticide O,S-dimethylphosphoroamidothioate, the preparation of which is disclosed in U.S. Pat. No. 3,309,226.

The paraffinic hydrocarbon component of the present invention is a viscous oil of the type described in the previously mentioned Volck oil patents U.S. Pat. Nos. 1,707,465 through 1,707,468. The hydrocarbon component desirably is a heavy oil, and thus its boiling range is typically determined at reduced pressure. Desirably, its boiling range at 10 mm Hg absolute pressure is substantially in the range 350° to 950° F., and preferably substantially in the range 660° to 860° F. By "substantially in the range" is meant that at least 80 percent boils within the specified range. In determining boiling ranges of oils, it is common to have small amounts uncharacteristic of the main fraction of oil which may boil off easily near the beginning boiling range of the fraction or which may trail off over a long range of temperature near the end of the boiling range of the fraction, thus ranges such as the 10% boiling point and the 90% boiling point are frequently used to substantially describe the boiling range character of a given fraction.

An important aspect of the present invention is the inclusion in the acephate or acephatemet/paraffinic oil formulation of a bridging component selected from isopropyl alcohol, secondary butyl alcohol, tertiary butyl alcohol, or methylene chloride. Acephate and acephatemet are extremely soluble in water but very insoluble in paraffinic oils. They are chemically unstable in the presence of water.

Among other factors, the present invention is based on my finding that the bridging component as specified above results in an unexpectedly well-solubilized mixture of the acephate or acephatemet and paraffinic hydrocarbon component, as well as a reasonably chemically stable mixture.

According to a preferred embodiment of the present invention, one or more of the three mentioned alcohol bridging components is used as the bridging component. I have found that these particular alcohols are exceptionally effective for good solublization of the particular mixture at hand, while still obtaining a good chemical stability for the mixture. Good chemical stability is, of course, important as it is desired that the formulation not degrade but instead retain a high degree of insecticidal efficacy. Using certain other alcohols, for example, n-butyl alcohol or n-propyl alcohol, was found to result in low stability for the insecticidal formulation.

The terms "insecticide" and "insect" as used herein refer to their broad and commonly understood usage rather than to those creatures which in the strict biological sense are classified as insects. Thus, the term "insect" is used not only to include small invertebrate animals belonging to the class Insecta but also to other related classes of arthropods whose members are segmented invertebrates having more or fewer than six legs, such as spiders, mites, ticks, centipedes, worms and the like.

Preferred amounts for the components of the insecticidal formulation of the present invention are as follows, expressed as weight percent of the entire formulation: Acephate or acephatemet, 0.01 to 10%, more preferably 4 to 8%; paraffinic hydrocarbon component, 0.01 to 30%, more preferably 15 to 25%; and for the bridging component 15 to 99.5%, more preferably 30 to 97%.

It is particularly preferred that the hydrocarbon component have an unsulfonated residue above about 90 weight percent.

Preferred bridging components for the formulation particularly include the specified alcohols, and of these alcohols isopropyl alcohol is especially preferred.

According to an alternate embodiment of the present invention, the formulation comprises four fundamental components. In this embodiment, the additional component is a secondary solvent component such as methylene chloride or a kerosene oil cut.

Methylene chloride is unique in that it can be used in the present formulation as a bridging component, but alternatively it can be used as a secondary solvent in the place of a material such a kerosene cut.

The kerosene cut which may be used as the secondary solvent desirably has a normal boiling range substantially within the range of about 350° to 550° F. The use of the term "normal" boiling range is used to mean boiling range at atmospheric pressure. As before, the use of the term "substantially" within the range is used to mean at least 80% of the secondary solvent hydrocarbon component boils within the specified range. Preferably the range for the kerosene secondary solvent is about 400° to 500° F. and for particularly preferred kerosene secondary solvents, essentially all of the solvent boils within the range of about 400° to 500° F., that is, the initial boiling point would be about 370° to 420° F. and the end point would be about 480° to 520° F.

Preferably the secondary solvent has an unsulfonated residue of at least 90%, more preferably at least 95 weight percent.

The test for unsulfonated residue of the secondary solvent or for the paraffinic heavy oil component of the formulation of the present invention is determined in accordance with ASTM method D483-63. In summary, according to ASTM method D483-63, a measured volume of sample is shaken with 98.61% sulfuric acid at 100° C. in a Babcock bottle, shaking mechanically for 10 seconds at 10-minute intervals. The volume not absorbed by the acid is a measure of the unsulfonated residue in the sample.

Other preferred characteristics for the secondary solvent include: moderate to low flammability; chemical compatability with the water-soluble insecticidal component; good solvency toward both the water-soluble insecticidal component and the paraffinic oil; and low human and animal toxicity.

Preferred amounts of the four fundamental components for the formulation in accordance with this embodiment of the invention, expressed as weight percent of the entire formulation, are as follows: acephate or acephatemet, 0.01 to 10%, more preferably 5 to 10%; paraffinic hydrocarbon component, 0.01 to 30%, more preferably 15 to 25%; secondary solvent component, 5 to 65%, more preferably 5 to 30%; and bridging component, 15 to 99.5%, more preferably 25 to 99.5%, and most preferably 30 to 97%.

Particularly preferred formulations in accordance with the present invention having either the three fundamental or four fundamental components are those wherein the acephate or acephatemet component is acephate.

Other ingredients which may be included in the formulation of the present invention include the following:

(a) emulsifiers, preferably ethoxylated alkylphenols, fatty esters, alkylglycol ethers, etc.;
(b) perfumes;
(c) oxidation inhibitors, preferably hindered phenols (BHT, BHA), hindered amines; hydroquinones, etc.;
(d) secondary toxicants, i.e., Kelthane insecticide, pyrethrins, synthetic pyrethrines, etc.

EXAMPLES

EXAMPLES 1-5

These examples illustrate the chemical stability or instability of acephate with certain alcohols. The procedure used to obtain the data for these examples was to combine acephate with the alcohol and then store the combined mixture, with one portion being stored at room temperature and another portion being stored at 100° F. After a period of time, the mixtures were analyzed by gas liquid chromatography to ascertain the amount of the active ingredient, that is, the acephate remaining undegraded. In the first four examples, 20 parts by weight of the acephate were combined with 80 parts by weight of the alcohol. In the fifth example, four parts by weight of the acephate were combined with 96 parts by weight of the alcohol.

In all cases, the mixtures were stored in sealed glass ampules.

The results of the stability test are reported in Tables I to V.

As can be seen for the isobutyl alcohol (2-methyl propanol), after 33 months at room temperature, only 72% of the active ingredient remained. At 100° F., only 49% of the active ingredient remained after 10.4 months.

For normal butyl alcohol after 33 months of storage at room temperature, only 66% of the active ingredient remained, and after 10.4 months of storage at 100° F., only 43% of the active ingredient remained undergraded.

These results from the first two tables can be contrasted to the results of Tables III, IV and V, wherein over 90% of the active ingredient remained after 33 months of storage at room temperature using the three alcohols which are used in the formulation of the present invention. Also, at the elevated temperature of 100° F., 70% percent or more of the active ingredient remained after about 10 months of storage.

TABLE I $$\text{CH}_3-\overset{\overset{\displaystyle CH_3}{|}}{\underset{\underset{\displaystyle CH_3}{|}}{CH}}-CH_2-OH$$

| Active | % Active Found | | Months |
|---|---|---|---|
| | Room Temp. | 100° F. | On Test |
| Acephate | 100 | — | 0 |
| Acephate | 96 | 100 | 1.2 |
| Acephate | 100 | 81 | 3.9 |
| Acephate | 95 | 49 | 10.4 |
| Acephate | 72 | | 33.0 |

TABLE II $$CH_3CH_2CH_2CH_2-OH$$

| Active | % Active Found | | Months |
|---|---|---|---|
| | Room Temp. | 100° F. | On Test |
| Acephate | 100 | — | 0 |
| Acephate | 100 | 95 | 1.2 |
| Acephate | 99 | 77 | 3.9 |
| Acephate | 93 | 43 | 10.4 |
| Acephate | 66 | | 33.0 |

TABLE III $$\underset{CH_3}{\overset{CH_3CH_2}{\diagdown}}CH-OH$$

| Active | % Active Found | | Months |
|---|---|---|---|
| | Room Temp. | 100° F. | On Test |
| Acephate | 100 | — | 0 |
| Acephate | 91 | 100 | 1.2 |
| Acephate | 100 | 93 | 3.9 |
| Acephate | 99 | 70 | 10.4 |
| Acephate | 93 | | 33.0 |

TABLE IV

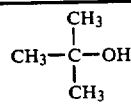

| Active | % Active Found Room Temp. | 100° F. | Months On Test |
|---|---|---|---|
| Acephate | 100 | — | 0 |
| Acephate | 100 | 100 | 1.2 |
| Acephate | 96 | 97 | 3.9 |
| Acephate | 92 | 71 | 10.4 |
| Acepahte | 99 |  | 33.0 |

TABLE V

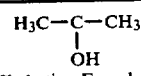

| Active | % Active Found Room Temp. | 100° F. | Months On Test |
|---|---|---|---|
| Acephate | 100 | — | 0 |
| Acephate | 100 | 89 | 8.0 |
| Acephate | 97 |  | 40.6 |

EXAMPLE 6

In this example, a mixture containing acephate and an oil component was prepared as follows: 2.88 g of acephate (97% purity) was blended with 81.17 g anhydrous isopropanol, 15.00 g Spray Oil 70/100, 0.75 g of nonionic emulsifier (nonyl phenol ethoxylate containing 9-10 mols of ethylene oxide), 0.10 g of 3,5-di-t-butyl-4-hydroxy toluene and 0.10 g perfume. The resulting mixture was a homogenous solution.

The Spray Oil 70/100 used in the above formulation had the following characteristics (ASTM Designation for Test Method given in parentheses):

|  | Min. | Max. | Typical Test Values |
|---|---|---|---|
| Gravity, °API (D-287) | 33.5 | 33.5 | 34.5 |
| Pounds per gallon at 68° F. |  |  | 7.07 |
| Unsulfonated Residue, Vol. % (D-483) | 93.0 |  | 93-95 |
| Viscosity (D-88) SSU @ 100° F. | 70.0 | 74.0 | 71.4 |
| Viscosity Index | 90.0 |  | 119 |
| Flash Point, COC, °F. (D-97) | 345.0 |  | 355 |
| Pour Point, °F. (D-97) |  | +10 | +5 |
| Color, ASTM (D-1500) |  | 0.5 | 0.5 |
| Aniline Point, °F. (D-611) |  |  | 199.6 |
| Refractive Index, $n_D^{20}$ |  |  | 1.4724 |
| Average Molecular Weight, |  |  | 319 |
| Carbon Atom Analysis |  |  |  |
| (ndM Method, ASTM D3238-74) |  |  |  |
| %$C_A$ |  |  | 4.5 |
| %$C_N$ |  |  | 33.5 |
| %$C_P$ |  |  | 62.0 |
| Distillation, °F., Vol. % |  |  |  |
| (D-1160 10 mm Hg) |  |  |  |
| Recovered |  |  | 98.0 |
| 50% Point | 427.0 | 437.0 | 436.0 |
| 10-90% Range |  | 80.0 | 60.0 |

EXAMPLE 7

In this example, a mixture containing acephate and a secondary solvent, namely a kerosene hydrocarbon fraction, was prepared as follows: 2.88 g of acephate (97% purity) was blended with 61.42 g anhydrous isopropanol, 10.00 g odorless kerosene, 25.00 g Spray Oil 70/100, 0.50 g nonionic emulsifier (as per Example 6), 0.10 g 3,5-di-butyl-7-hydroxy-toluene and 0.10 g perfume. The resulting product was a clear homogenous solution.

The odorless kerosene used in the above example has the following characteristics:

| Properties | Test Method | Min. | Max. |
|---|---|---|---|
| Gravity, °API | ASTM D-287 | 43.0 |  |
| Flash Point, TCC, °F. | ASTM D-56 | 125 |  |
| Fire Point, TOC, °F. | SM 105-4 | 130 |  |
| Color, Saybolt | ASTM D-156 | +25 |  |
| Doctor Test | ASTM D-484 | Neg. |  |
| Distillation, °F.: | ASTM D-86 |  |  |
| IBP |  | 350 | 375 |
| EP |  | 460 | 510 |
| Cloud Point, °F. | ASTM D-2500 |  | 5 |
| Odor | SM 165-3 | Equal to Standard |  |
| Odor, Residual | VV-K-220A | None |  |
| U.V. Absorbance per cm path Millimicrons | SM 20-36 |  |  |
| 280-289 |  |  | 4.0 |
| 290-299 |  |  | 3.3 |
| 300-329 |  |  | 2.3 |
| 330-360 |  |  | 0.8 |
| Chlorine, mg per g | ASTM D-808 |  | 0.1 |
| Unsulfonated Residue, vol.% | ASTM D-483 | 96.0 |  |
| General |  | Shall be practically odorless and contain no foreign matter, water, etc. |  |

EXAMPLE 8

In this example, acephate was mixed with a large amount of the hydrocarbon component, namely 25 weight percent of a Volck oil, and only marginally satisfactory to unsatisfactory mixing was obtained without the use of a secondary solvent. This preparation was prepared as follows: 8.25 g of acephate (97% purity) was blended with 64.75 g anhydrous isopropanol, 25.00 g Spray Oil 70/100 and 2.00 g of a nonionic emulsifier (see description of Example 6).

EXAMPLES 9-11

In these examples, a fourth fundamental component was used in preparation of the insecticidal formulation, namely a secondary solvent, which was methylene chloride.

|  | Ex. 9 | Ex. 10 | Ex. 11 |
|---|---|---|---|
| Acephate, 97% purity | 8.25 g | 8.25 g | 8.25 g |
| nonionic emulsifier* | 2.00 | 2.00 | 2.00 |
| Anhydrous isopropanol | 52.10 | 38.95 | 19.20 |
| Methylene chloride | 12.65 | 25.80 | 45.50 |
| Spray Oil 70/100 | 25.00 | 25.00 | 25.00 |

*Nonyl phenol ethoxylate (9-10 mols ethylene oxide)

All materials were blended together to form clear, homogenous solutions at 20° C.

EXAMPLE 12

In this preparation, 0.064 g acephate (97%) was blended with 99.536 g anhydrous isopropanol alcohol and 0.400 g Spray Oil 70/100, yielding a uniform solution to be used as a "Ready-to-Spray" product. This product does not contain emulsifiers and is not mixed with water prior to application.

What is claimed is:

1. An insecticidal formulation comprising 0.01 to 10 weight percent of acephate or acephatemet component, 0.01 to 30 weight percent of, a paraffinic hydrocarbon component having a boiling range at 10 mm Hg absolute pressure substantially within the range of 550° to 950° F. and an unsulfonated residue above about 85 weight percent; and a bridging component in an amount effective to form a solution containing the aforesaid two components, wherein the bridging component is isopropyl alcohol, secondary butyl alcohol, tertiary butyl alcohol, or methylene chloride.

2. A formulation in accordance with claim 1 wherein the amounts of the components are as follows expressed as weight percent of the entire formulation:
   acephate or acephatemet: 4 to 8 percent
   paraffinic hydrocarbon component: 15 to 25 percent
and wherein the hydrocarbon component has an unsulfonated residue above 90 weight percent.

3. A formulation in accordance with claim 2 wherein the acephate or acephatemet component is acephate and the paraffinic hydrocarbon component has a boiling range at 10 mm Hg absolute pressure substantially within the range of 660° to 860° F.

4. A formulation in accordance with claim 1 wherein the bridging component is secondary butyl alcohol, tertiary butyl alcohol, or isopropyl alcohol.

5. A formulation in accordance with claim 4 wherein the bridging component is isopropyl alcohol.

6. An insecticidal formulation comprising 0.01 to 10 weight percent of acephate or acephatemet component, 0.01 to 30 weight percent of; a paraffinic hydrocarbon component having a boiling range at 10 mm Hg absolute pressure substantially within the range of 550° to 950° F. and an unsulfonated residue above about 85 weight percent, a secondary solvent hydrocarbon compontent having a normal boiling range substantially within the range 350° to 550° F. and an unsulfonated residue above about 85 weight percent; and a bridging component in an amount effective to form a solution containing the aforesaid components, wherein the bridging component is isopropyl alcohol, secondary butyl alcohol, tertiary butyl alcohol, or methylene chloride.

7. A formulation in accordance with claim 6 wherein the amount of the components is as follows expressed as weight percent of the entire formulation:
   acephate or acephatemet: 0.01 to 10 percent
   paraffinic hydrocarbon component: 0.01 to 30 percent
   secondary solvent: 5 to 65 percent.

8. A formulation in accordance with claim 7 wherein the amount of the components is as follows expressed as weight percent of the entire formulation:
   acephate or acephatemet: 5 to 10 percent
   paraffinic hydrocarbon component 15 to 25 percent
   secondary solvent: 5 to 30 percent.

9. A formulation in accordance with claim 8 wherein the acephate or acephatemet component is acephate and the paraffinic hydrocarbon component has a boiling range at 10 mm Hg absolute pressure substantially within the range of 660° to 860° F.

* * * * *